United States Patent [19]

Binderup

[11] 4,259,333
[45] Mar. 31, 1981

[54] CEPHALOSPORINES

[75] Inventor: Ernst T. Binderup, Tåstrup, Denmark

[73] Assignee: Leo Pharmaceutical Products Ltd. A/S (Lovens Kemiske Fabrik Produktionsaktieselskab), Ballerup, Denmark

[21] Appl. No.: 949,111

[22] Filed: Oct. 6, 1978

[30] Foreign Application Priority Data

Oct. 28, 1977 [GB] United Kingdom ............... 45107/77
Dec. 20, 1977 [GB] United Kingdom ............... 53064/77

[51] Int. Cl.$^3$ ................... C07D 501/36; C07D 501/20
[52] U.S. Cl. ....................................... 424/246; 544/16; 544/27; 544/22; 544/21; 544/28; 542/420
[58] Field of Search ................. 260/306.7 C; 424/246; 544/16, 27, 22, 21, 28, 30; 542/420

[56] References Cited

U.S. PATENT DOCUMENTS 3,821,198  6/1974  Lee et al. ................... 544/30

FOREIGN PATENT DOCUMENTS 2430375  3/1975  Fed. Rep. of Germany .

Primary Examiner—Nicholas S. Rizzo
Attorney, Agent, or Firm—Cushman, Darby & Cushman

[57] ABSTRACT

Substituted 7β-amidino-Δ$^3$-cephem-4-carboxylic acids, pharmaceutically acceptable, non-toxic salts and esters thereof, antibacterial compositions containing these compounds and methods and methods of using the same against infection diseases.

25 Claims, No Drawings

CEPHALOSPORINES

The present invention relates to new substituted 7β-amidino-Δ³-cephem-4-carboxylic acids; to pharmaceutically acceptable, non-toxic salts and esters and pharmaceutically acceptable, non-toxic salts of such esters; to methods of producing these compounds; to new intermediates for their preparation, to pharmaceutical compositions containing the compounds; to dosage units thereof; and to their use in human and veterinary therapy.

The compounds of the invention are represented by the general formula I

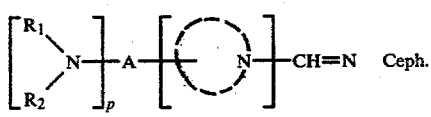

in which the radical

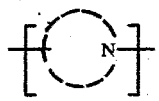

stands for the groupings:

representing saturated, monocyclic, bicyclic or spirocyclic ring systems, respectively, containing from 4 to 11 carbon atoms in total; -A- stands for a straight or branched, saturated or unsaturated $C_1$ to $C_6$ aliphatic hydrocarbon radical optionally containing an aryl moiety, and where -A- optionally can be substituted with an amino radical; $R_1$ stands for hydrogen, or a lower alkyl radical with from 1 to 4 carbon atoms; $R_2$ stands for hydrogen, a lower alkyl radical or a monoacyl radical derived from a mono- or dibasic carboxylic acid, sulphuric acid, a sulphonic acid, a sulphinic acid, phosphoric acid, or a phosphonic acid, and $R_2$ can represent an unsubstituted or substituted carbamoyl, guanyl and guanylcarbamoyl radical; $R_1$ and $R_2$ together with the nitrogen atom can form a monocyclic, saturated ring having from 4 to 8 carbon atoms or an azido group; furthermore $R_1$ and $R_2$ together can represent a radical of the formula

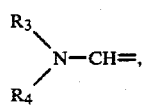

in which $R_3$ and $R_4$ each stands for hydrogen, lower alkyl, aryl or aryl-lower-alkyl, or in which $R_3$ and $R_4$ together with the nitrogen atom form a monocyclic, saturated ring having from 4 to 8 carbon atoms; p is 1, and when A contains an aryl moiety p is 0 or 1; Ceph. stands for the Δ³-cephem-4-caboxylic acid radical of the formula III

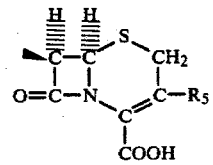

in which $R_5$ is halogen, methoxy or the group —CH=CH—COOH, or a $CH_2R'_5$ group representing any substituents known in the 3-position of the 7-acylamino-Δ³-cephem-4-carboxylic acid series, $R'_5$ being e.g. hydrogen, halogen, hydroxy, alkoxy, an acyloxy radical, a carbamoyloxy radical optionally substituted at the nitrogen atom, an alkylthio radical, a heterocyclylthio radical, a trialkylammonium radical, a pyridinium radical optionally substituted in the ring, a thiuronium group, an amidinothio radical optionally substituted at the nitrogen atoms with $C_1$ to $C_3$ alkyl groups, a N-substituted aminothiocarbonylthio radical, an arylthio radical, an alkoxythio-carbonylthio radical, an alkylarylsulfonyl radical, an azido, amino or an amido group, a polyhydroxyphenyl radical, an indol-3-yl radical optionally substituted at the nitrogen atom with $C_1$ to $C_3$ alkyl groups, or a thiocyano radical.

The invention also comprises salts of the compounds of the formula I with pharmaceutically acceptable, non-toxic, organic and inorganic acids or bases, and pharmaceutically acceptable, non-toxic, esters of the compounds of formula I including diesters of the formula IV:

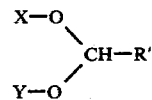

in which X and Y can be the same or different and stand for an acyl radical of one of the compounds of formula I, and Y furthermore can be the acyl radical of other known β-lactam derivatives, R' stands for hydrogen, methyl, ethyl, or phenyl; and salts of such esters with pharmaceutically acceptable, non-toxic acids or bases.

More particularly, -A- represents straight or branched aliphatic radicals such as methylene, ethylene, ethylidene, propylene, trimethylene, tetramethylene, propylidene, methyltrimethylene, pentamethylene, methyltetramethylene, dimethyltrimethylene, hexamethylene, ethyltetramethylene, methylpentamethylene, or unsaturated aliphatic radicals such as propenylene, butenylene, pentenylene; hexenylene; hexadienylene; methylpropenylene, dimethylpropenylene, propynylene, butynylene, hexynylene; methylpropynylene, methylpentynylene, 2-penten-4-ynylene and 1-methyl-2-penten-4-ynylene, the aryl moiety can preferably be phenyl or lower alkyl-, lower alkoxy- and halogen- or trifluoromethyl- substituted phenyl, in which case -A- may e.g. represent phenylmethylene, β-phenylethylene, or:

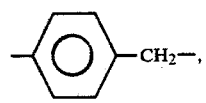

the above examples, however, not to be construed as limiting the invention.

-A- may optionally be substituted with an amino radical which can be an unsubstituted or a mono- or dilower alkyl substituted amino group or a lower alkanoyl substituted amino group placed on the aliphatic chain or on the aryl moiety.

More particularly, $R_1$ can be hydrogen or a lower alkyl radical having from 1 to 4 carbon atoms as, for instance, methyl, ethyl, propyl, isopropyl, n-butyl, sec-butyl, isobutyl or tert-butyl.

Similarly, $R_2$ stands for hydrogen or a lower alkyl radical as defined for $R_1$, or $R_2$ stands for an acyl radical as, for instance, formyl, acetyl, propionyl, butyryl, isobutyryl, valeryl, isovaleryl, trimethylacetyl, caproyl, crotonyl, glycolyl, benzoyl, phenylacetyl, phenoxyacetyl, glycyl, phenylglycyl or acyl radicals of other amino acids, heterocyclically substituted acyl, e.g. nicotinoyl or

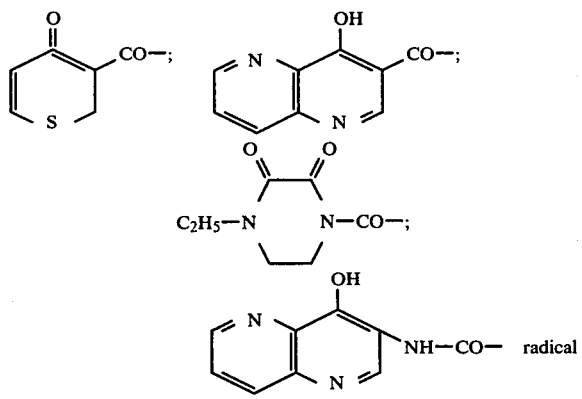

or a monoacyl radical derived from a dibasic acid such as oxalic, malonic, succinic, maleic, fumaric, tartaric, malic or phthalic acids; and when $R_2$ stands for a substituted carbamoyl, guanyl, or guanylcarbamoyl radical, the substituents can be e.g. lower alkyl or phenyl radicals. Further $R_2$ stands for an acyl radical derived from sulphuric acid, a sulphonic, sulphinic, phosphoric or a phosphonic acid such as toluenesulphonic acid, methane- or ethanesulphonic acid, toluenesulphonic acid, lower alkylphosphonic acids etc.

In the formula above $R_3$ and $R_4$ can more specifically be lower alkyl with from 1 to 4 carbon atoms or phenyl-lower alkyl in which the alkyl radical has from 1 to 4 carbon atoms. When $R_1$ and $R_2$, or $R_3$ and $R_4$ together with the nitrogen atom form a ring system this may be a pyrrolidyl, piperidyl, hexahydro-1H-azepin-1-yl or octahydro-azocin-1-yl radical.

The radicals $R_1$ and $R_2$ may be further substituted with a halogen atom, halo-alkyl, including trifluoromethyl, hydroxy, alkoxy, alkylthio group, an acyl group, a carboxy, carbalkoxy, carbamyl, carbamido, cyano or sulphonyl group, an amino- or substituted amino group.

More particularly, $R_5$ when representing halogen can be chlorine, bromine or fluorine; and $R'_5$ is hydroxy, alkoxy, e.g. methoxy; a lower alkanoyloxy e.g. acetoxy; carbocyclic or heterocyclic aroyloxy, e.g. benzoyloxy, aralkanoyloxy, e.g. phenylacetoxy; α-methoxy-p-sulphoxycinnamoyloxy; or an α-methoxy-p-hydroxycinnamoyloxy radical; a carbamyloxy radical of the formula —OOCNR$_6$R$_7$, wherein $R_6$ and $R_7$ each can be hydrogen, lower alkyl, halo-lower alkyl, lower alkoxy-carbonyl, aryl e.g. phenyl, alkarylsulphonyl, e.g. p-toluenesulphonyl, benzhydryl, or taken together with the nitrogen atom to which they are bonded a heterocyclic radical, chosen from the group consisting of pyrrolidinyl, piperidyl and morpholinyl; further $R'_5$ may be a thio radical of the formula —SR$_8$, in which $R_8$ represents lower alkyl, aryl, heterocyclic radical chosen from the group consisting of pyridyl, lower alkyl-thiazolyl, 1,3,4-thiadiazol-2-yl, 5-alkyl-1,3,4-thiadiazol-2-yl, or a 1-substituted 1,2,3,4-tetrazol-5-yl derivative of the formula

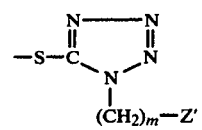

in which Z' stands for —COOH, —SO$_3$H, —CONH$_2$, —SO$_2$NH$_2$, —OH, amino or substituted amino, —H; and m is an integer having the value from one to five, such as 1-carboxymethyl-1,2,3,4-tetrazol-5-yl, 1-sulphomethyl-1,2,3,4-tetrazol-5-yl, 1-methyl-1,2,3,4-tetrazol-5-yl, 1-dimethylaminoethyl-1,2,3,4-tetrazol-5-yl, 1,2,3-triazol-5-yl, 2-benzothiazolyl, and 4-lower alkyl-pyrimidinyl-2; $R_5'$ may further be alkanoyl, aralkanoyl or carbocyclic or heterocyclic arylcarbonyl tri(lower alkyl)-ammonium; a pyridinium radical of the formula

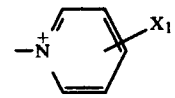

in which $X_1$ is hydrogen, halogen or a trifluoromethyl, nitrocyano, carboxy, carbamyl, N-lower alkyl-carbamyl, N,N-dilower alkylcarbamyl, carboxymethyl, lower alkanoyl, lower alkyl, hydroxymethyl or sulpho radical; furthermore R'$_5$ may be a thiuronium radical, an amidinothio radical of the formula

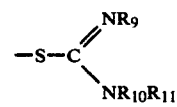

in which R$_9$, R$_{10}$, and R$_{11}$ are hydrogen or lower alkyl having from 1 to 3 carbon atom, an aminothiocarbonylthio radical of the formula

in which R$_{12}$ and R$_{13}$ represent hydrogen, a lower alkyl, hydroxy-lower alkyl, di-(lower alkyl)-amino-lower alkyl, morpholino-lower alkyl, N-aryl-N-lower alkyl-aminoalkyl radical, or taken together with the nitrogen atom to which they are bonded, a heterocyclic radical chosen from the group consisting of morpholinyl, piperidyl, pyrrolidyl or a piperazinyl radical of the formula

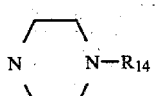

in which $R_{14}$ is lower alkyl or phenyl, furthermore $R'_5$ can be an alkoxythiocarbonylthio radical of the formula

in which $R_{15}$ is lower alkyl or lower cycloalkyl, $R'_5$ can also be alkarylsulphonyl, azido, or a radical of the formula

in which $R_{16}$ is hydrogen or an alkyl radical, and $R_{17}$ is hydrogen, aryl, lower alkanoyl, aralkanoyl, or $R_{16},R_{17}$-N is an imidazole or alkyl imidazole radical; $R'_5$ may further be a polyhydroxyphenyl radical, a N-lower-alkyl-indol-3-yl, or a thiocyano radical; or radicals of the formulae

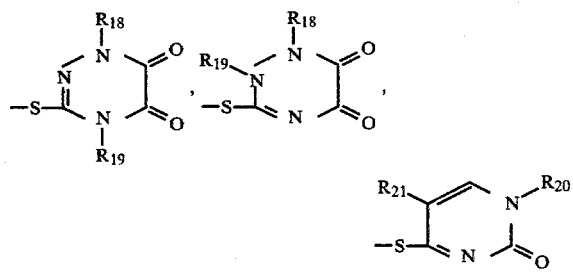

in which one of the groups $R_{18}$ and $R_{19}$ is hydrogen or alkyl and the other is alkyl, $R_{20}$ is amino, alkyl or alkoxy and $R_{21}$ is hydrogen or alkyl. Whereever the terms alkyl, alkoxy or alkanoyl are used without further definition they shall mean to have from 1 to 4 carbon atoms, e.g. methyl, ethyl, propyl, isopropyl, n-butyl; methoxy, ethoxy, propoxy, isopropoxy, n-butoxy; acetyl, n-propionyl.

More particularly the groupings:

representing saturated monocyclic, bicyclic or spirocyclic ring systems can be pyrrolidyl, piperidyl, hexahydro-1H-azepinyl, octahydro-azocinyl, decahydro-azecinyl, azacyclododecanyl, 3-azabicyclo[3.1.0]hexanyl, 5-azaspiro[2.4]heptanyl, 3-azabicyclo[4.1.0]heptanyl, 3-azabicyclo[3.2.0]heptanyl, 6-azabicyclo[3.1.1]heptanyl, 7-azabicyclo[4.2.0]octanyl, 2-azabicyclo[2.2.2]octanyl, 1-azaspiro[5.5]undecanyl, 2-, and 3-azabicyclo[3.3.1]nonanyl 2-azaspiro[4.6]undecanyl, 2-azabicyclo[3.2.1]octanyl, 3-azabicyclo[3.2.1]octanyl, 6-azabicyclo[3.2.1]octanyl, 1-azaspiro[4.5]decanyl, 2-azaspiro[4.5]decanyl, 2-azabicyclo[3.2.2]nonanyl, 3-azabicyclo[4.1.1]octanyl, 2-azabicyclo[2.2.1]heptanyl, 2-azabicyclo[4.3.1]decanyl, 8-azaspiro[4.5]decanyl, 2-azaspiro[5.5]undecanyl, 3-azaspiro[5.5]undecanyl, 3-azabicyclo[3.1.1]heptanyl, 2-azabicyclo[4.2.0]octanyl, 2-azaspiro[4.4]nonanyl, 8-azabicyclo[4.3.1]decanyl, 4-azabicyclo[5.3.0]decanyl, 3-azabicyclo[3.3.0]octanyl, 8-azabicyclo[4.3.0]nonyl, the examples above, however, not being construed as limiting the invention.

The compounds of formula I may be isolated as such or in the form of a salt with a pharmaceutically acceptable, non-toxic acid, such as hydrochloric acid, phosphoric acid, nitric acid, p-toluenesulphonic acid, acetic acid, acid, propionic acid, citric acid, tartaric acid, maleic acid, etc. Alternatively the compounds of formula I may be isolated as the zwitterion (amphoion) or as a salt with a base e.g. the alkali metal salts and alkaline earth metal salts, for example sodium, potassium, magnesium or calcium salts, as well as salts with ammonia or suitable non-toxic amines, such as lower alkyl amines, for example triethylamine, hydroxy-lower alkylamines, for example 2-hydroxyethylamine, bis-(2-hydroxyethyl)-amine, or tris-(2-hydroxyethyl)-amine, cycloalkylamines, for example dicyclohexylamine, or benzylamines, for example N,N'-dibenzyl-ethylenediamine, and dibenzylamine, without these examples being limiting the invention. Thus for instance other antibiotics with acid or basic character can be used as components of such salts of the compounds of formula I.

The esters of the compounds of formula I are such in which the hydrogen atom of the carboxylic group is substituted by an alkyl radical, or an aralkyl radical, preferably a lower alkyl and aryl-lower alkyl radical, or an alkyl radical substituted with halogen, or cyano; e.g. methyl, ethyl, tert.butyl, benzyl, diphenylmethyl or triphenylmethyl, chloro-methyl, $\beta,\beta,\beta$-trichloroethyl, or cyanomethyl; an acyloxyalkyl radical the acyl part of which being a lower aliphatic, or aromatic, carboxylic radical, such as acetyl, propionyl, butyryl, pivaloyl, benzoyl etc., and the alkyl part being preferably methyl and ethyl; or an alkoxycarbonyloxyalkyl radical, e.g. a methoxy- or ethoxycarbonyloxymethyl radical or one of the corresponding -oxyethyl radicals; or lactonyl esters, e.g. a phthalidyl radical; or the acyl group of such acyloxyalkyl esters can be derived from a $\beta$-lactam antibiotic, such as a penicillin, a cephalosporin, a 6-amidinopenicillanic or 7-amidino-$\Delta^3$-cephem-4-carboxylic acid or other $\beta$-lactam derivatives, e.g. clavulanic acid, which by competitive inhibition can protect $\beta$-lactam antibiotics against the activity of $\beta$-lactamases.

When the side chain or the ester group contain one or more asymmetric carbon atoms or double bonds giving rise to cis-trans isomerism the compounds of formula I and their esters exist in several diastereomeric forms. The invention comprises all of these forms as well as mixtures thereof. The $\Delta^3$-cephem-4-carboxylic acid moiety has the steric configuration indicated in the formula III.

For certain medical purposes it will be advantageous to use the free acids or their salts. For other purposes it will be advantageous to use the esters of the compounds of formula I, e.g. in order to obtain a specific distribution in the body.

In particular, it can be advantageous to apply the aforementioned easily hydrolyzable esters which usually are readily absorbed after oral administration. Such esters are in the body hydrolyzed under the influence of enzymes present in blood and tissues with liberation of the corresponding free acids.

Appropriately the esters above can be prepared and used in the form of their salts with pharmaceutically acceptable, non-toxic, inorganic or organic acids.

A series of substituted 7β-amidino-Δ³-cephem-4-carboxylic acids, their salts and esters are disclosed in the German Patent Application DOS No. 2430375.1.

The compounds of the present invention are active against a variety of microorganisms, in particular pathogenic gram positive and gram negative bacteria. Of special interest in this connection is the activity towards certain gram negative bacteria.

They are also capable of potentiating the activity of other β-lactam antibiotics, including penicillins, cephalosporins and amidinopenicillanic acids.

Within the scope of this invention are compounds in which -A- stands for a saturated or unsaturated carbon chain with from 1 to 6 carbon atoms, p is 1 and $R_1$ and $R_2$ stand for hydrogen and in which the radicals of formula II have from 5 to 8 carbon atoms in the

grouping and a maximum of 7 carbon atoms in the individual rings of the bicyclic and spirocyclic groupings

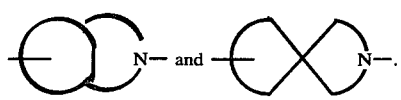

Generally, such compounds are preferred in which the carbon chain -A- is not attached to a carbon atom adjacent to the nitrogen atom of the monocyclic ring system.

The table below indicates compounds of the invention corresponding to formula I in which p is 1 and $R_1$, $R_2$, -A- and the numbers of the carbon atoms (n) in the ring

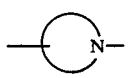

are as follows:

| $R_1$ | $R_2$ | -A- | n |
|---|---|---|---|
| H | H | propylene | 4 |
| H | acetyl | trimethylene | 4 |
| ethyl | H | tetramethylene | 4 |
| methyl | propionyl | 1,1-dimethylethylene | 4 |
| H | H | hexamethylene | 4 |
| butyl | butyl | 2-methyltetramethylene | 4 |
| methyl | H | 2-methylpentamethylene | 5 |
| H | guanyl | hexamethylene | 5 |
| H | butyryl | trimethylene | 5 |
| isopropyl | H | tetramethylene | 5 |
| H | H | 2-aminotetramethylene | 5 |
| H | acetyl | 2-acetaminotetramethylene | 5 |
| methyl | methyl | 2-dimethylaminotetramethylene | 5 |
| H | H | trimethylene | 5 |
| methyl | methyl | trimethylene | 5 |
| H | methyl | trimethylene | 6 |
| butyl | H | ethylene | 6 |
| H | H | ethylidene | 6 |
| methyl | tosyl | methylene | 6 |
| H | acetyl | methylene | 6 |
| H | H | 1-propanyl-3-ylidene | 5 |
| H | guanyl | butenylene | 6 |
| methyl | methyl | hexynylene | 5 |
| H | carbamoyl | ethylene | 6 |
| H | guanyl | methylene | 6 |
| methyl | guanyl | propylene | 6 |
| H | H | trimethylene | 7 |
| H | acetyl | 2-methyltrimethylene | 7 |
| methyl | methyl | tetramethylene | 7 |
| methyl | H | ethylene | 7 |
| H | H | methylene | 7 |
| H | carbamoyl | methylene | 7 |
| butyl | H | propylene | 7 |
| H | H | 2-aminopropylene | 7 |
| H | H | methylene | 8 |
| H | acetyl | ethylidene | 8 |
| H | guanyl | ethylene | 8 |
| methyl | H | ethylene | 8 |
| H | guanylcarbamoyl | ethylene | 8 |
| H | H | propylene | 8 |
| H | hemisuccinyl | ethylidene | 8 |
| H | methanesulphonyl | ethylene | 8 |
| H | tosyl | methylene | 9 |
| H | H | ethylene | 9 |
| H | H | methylene | 10 |
| methyl | H | methylene | 10 |
| H | acetyl | ethylene | 10 |
| H | H | methylene | 11 |
| methyl | methyl | methylene | 11 |

The table below indicates compounds of the invention corresponding to formula I in which p is 1, $R_1$, $R_2$, -A-, and the number of carbon atoms in the ring

are as follows, where $n_1$ refers to the heterocyclic part of the ring system, and $n_2$ refers to the total number of carbon atoms in the ring system.

| $R_1$ | $R_2$ | -A- | $n_1$ | $n_2$ |
|---|---|---|---|---|
| methyl | H | ethylene | 3 | 7 |
| H | H | methylene | 6 | 7 |
| H | H | 2-aminopropylene | 6 | 7 |
| H | propionyl | tetramethylene | 4 | 6 |
| ethyl | H | methylene | 4 | 7 |
| methyl | methyl | propylene | 5 | 7 |
| N,N-dimethylaminomethylene | | methylene | 6 | 9 |
| H | H | propenylene | 4 | 7 |
| ethyl | ethyl | hexenylene | 5 | 8 |
| H | carbamoyl | butynylene | 4 | 6 |

The table below indicates compounds of the invention corresponding to formula I in which p is 1, $R_1$, $R_2$, -A-, and the number of carbon atoms in the ring

are as follows, where $n_1$ refers to the heterocyclic part of the ring system, and $n_2$ refers to the total number of carbon atoms in the ring system.

| $R_1$ | $R_2$ | -A- | $n_1$ | $n_2$ |
|---|---|---|---|---|
| H | H | 1-aminopropylene | 4 | 9 |

| $R_1$ | $R_2$ | -A- | $n_1$ | $n_2$ |
|---|---|---|---|---|
| methyl | methyl | 1,1-dimethyl-ethylene | 4 | 9 |
|  | aminomethylene | methylene | 4 | 10 |
| methyl | H | ethylene | 5 | 10 |
| ethyl | ethyl | trimethylene | 5 | 10 |
| H | H | propenylene | 5 | 9 |

The compounds indicated in the foregoing tables have preferably in the cephem ring structure as the R'$_5$ substituent, hydrogen, acetoxy, 2-methyl-1,3,4-thiadiazol-5-yl-thio, 1-methyl-1H-tetrazol-5-yl-thio, 1,2,3-triazol-5-yl-thio, 5-methyl-1,3,4-thiadiazol-2-yl-thio, 1-pyridinium, azido, carbamyl, 1,2,5,6-tetrahydro-2-methyl-5,6-dioxo-as-triazin-3-ylthio or 1,4,5,6-tetrahydro-4-methyl-5,6-dioxo-as-triazin-3-yl-thio.

Interesting compound species of formula I are:
7-[4-(3-aminopropyl)-1-piperidyl-methyleneamino]-3-[[(1,2,5,6-tetrahydro-2-methyl-5,6-dioxo-as-triazin-3-yl)-thio]-methyl]-3-cephem-4-carboxylic acid
7-[4-(3-dimethylaminopropyl)-1-piperidyl-methyleneamino]-3-[[(1,2,5,6-tetrahydro-2-methyl-5,6-dioxo-as-triazin-3-yl)-thio]-methyl]-3-cephem-4-carboxylic acid
7-[(4-(2-aminoethyl)- and 7-[(4-(3-aminopropyl)-1-piperidyl)-methyleneamino]-3-carbamoyloxymethyl-3-cephem-4-carboxylic acid.

The above examples, however, shall in no way be construed as limiting the invention.

The invention also comprises methods for the preparation of the compounds of the invention. In one embodiment the compounds are prepared by reacting a reactive derivative of an amide or a thioamide of the general formula V

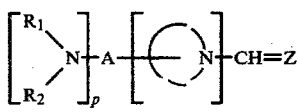
               V in which $R_1$, $R_2$, -a-, p and

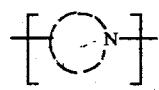

are as defined hereinbefore, or

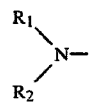

is, if necessary, protected or replaced by a nitro or an azido group, or a halogen atom, whereas Z stands for oxygen or sulphur, with a 7-amino-$\Delta^3$-cephem-4-carboxylic acid derivative of the general formula VI

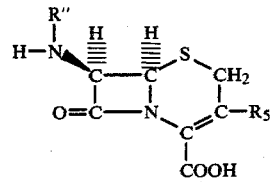
               VI in which R'' is hydrogen or a trialkylsilyl group, and $R_5$ is as defined above or a salt thereof, or with an ester of the intermediate of formula VI, e.g. a trialkylsilyl, tert-.butyl, benzyl or cyanomethyl ester or an easily hydrolyzable ester as defined above or an ester of the formula VII

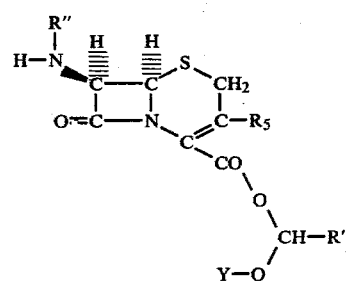
               VII in which R', R'', $R_5$ and Y have the meaning hereinbefore defined.

If a silyl ester of the intermediate of formula VI is used, the reaction must be followed by a hydrolysis or alcoholysis to provide the free acids of the invention, which also may be obtained by cleavage of the other esters obtained by the reaction.

The preparation of the above mentioned 7-amino-$\Delta^3$-cephem-4-carboxylic acid derivatives is known from the literature or the derivatives can be prepared by processes analogous to the known processes in the literature.

In the case where in the compounds of formula I, one or both of $R_1$ and $R_2$ stand for hydrogen or

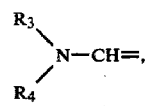

$R_3$ and/or $R_4$ being hydrogen, or if the carbon chain -A- is substituted with a reactive amino radical, it can be necessary to protect the

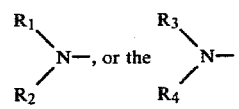

groupings, and, if present, the amino radical temporarily during the process with protecting groups more particularly described below. Alternatively, instead of the starting materials of formula V can be used a compound which instead of the

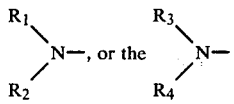, or the 

groupings and, if present, the amino radical has a group, e.g. a nitro or an azido group, or a halogen atom, which after the reaction with the compound of formula VI or VII can be transformed into an amino group under mild conditions. These intermediates thus obtained are also new compounds constituting as such a part of this invention. Also they have in themselves interesting antibacterial properties, especially the azido compounds, and also compounds in which the protecting group is a tert.butyloxycarbonyl group.

The starting materials of formula V can be prepared by conventional methods known to the man skilled in the art. The reactive derivatives of these starting materials are in the following described more in detail.

The amides or thioamides of formula V can be transformed by well-known methods into reactive derivatives such as acid amide halides or acid amide acetals or iminium-ethers or -thioethers, e.g. acid amide dialkyl sulphate complexes or complexes with the well-known Meerwein reagent (triethyloxonium tetrafluoroborate). The acid amide halides are preferably the chlorides or bromides and they can be prepared by treating the amides with halogenating agents. It is preferred to use halogenating agents which throughout the reaction form gaseous by-products, such as phosgene, oxalyl halides, or thionyl halides, but others may also be used. The reaction can be performed in an inert, dry, organic solvent, e.g. ether or toluene, in which the amide halide will in most cases be insoluble and from which it can be isolated by filtration after the reaction is completed. The acid amide halides are hygroscopic and rather unstable and are therefore preferably used in the next step without purification. However, the amide halide may also be prepared in e.g. alcohol-free chloroform solution and used directly for the next step, advantage being taken of the harmless character of the gaseous by-products (CO, $CO_2$, $SO_2$, COS).

Useful acid amide dialkyl sulphate complexes as intermediates can be prepared by treating the corresponding amides with a dialkyl sulphate, preferably dimethyl sulphate, under well-known conditions. By treating the acid amide dialkyl sulphate complexes or acid amide halides with a sodium $C_1$ to $C_6$ alcoholate, e.g. sodium methoxide, acid amide acetals of the general formula V(a)

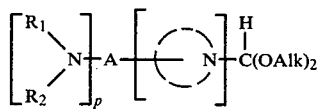 V (a)

in which $R_1$, $R_2$, -A-, p and the grouping

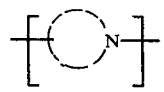

have the meaning hereinbefore defined, or is, if necessary, protected or replaced by a nitro or an azido group or a halogen atom, whereas Alk stands for an alkyl group containing 1 to 6 carbon atoms, are formed, which acetals may also be used in the preparation of compounds of formula I.

When acid thioamides are used as starting materials, a reactive derivative in form of an acid thioamide alkyl halide complex can be formed by treatment with an alkyl halide, e.g. a $C_1$ to $C_6$ alkyl iodide. This reaction is well known from the chemical literature.

The reaction conditions for the reaction between the amide derivative and the compound of formula VI or VII depend on the reaction components used in the process. For instance, when an acid amide acetal or a dialkyl sulphate complex or another iminium ether or thioether is used in the reaction with the compound of formula VI or VII, the reaction is performed in an organic solvent and at a temperature depending upon the reaction components. When an acid amide halide is used, the reaction is usually performed in an inert organic solvent, which is dry and free from traces of alcohol, preferably chloroform, in which the reaction components are soluble, but solvents in which the starting materials are insoluble, e.g. ether, may also be used. The reaction is performed with cooling and, if necessary, in the presence of at least one equivalent of a tertiary amine, for example trimethylamine, triethylamine, N,N-diisopropylethylamine or N-methylmorpholine.

The reaction time depends on the reactants, the temperature and the solvents used in the process.

The mono- or di-silyl esters of the 7-amino-$\Delta^3$-cephem-4-carboxylic acids can be prepared by a silylation of a 7-amino-$\Delta^3$-cephem-4-carboxylic acid with e.g. hexamethyldisilazane or trimethylchlorosilane, in the last case in the presence of a tertiary amine, and analogous to the preparation of the corresponding esters of 6-aminopenicillanic acid. The silyl esters of the amidino-$\Delta^3$-cephem-4-carboxylic acids are preferably cleaved by a hydrolysis or an alcoholysis under mild conditions.

In the preparation of compounds of formula I, it is also possible to use as starting material a trialkylammonium salt of 7-amino-$\Delta^3$-cephem-4-carboxylic acids which is reacted with e.g. an acid amide acetal under the same conditions as mentioned above. Such reactions are known from the specification to our British Pat. No. 1 417 099.

In another embodiment the compounds of the present invention can be prepared by reacting an amine of the formula VIII

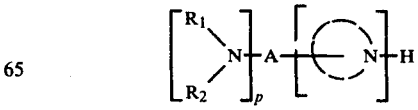 VIII in which $R_1$, $R_2$, -A-, p and the grouping

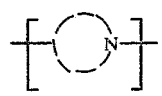

are as hereinbefore defined, or

is, if necessary, protected or replaced by nitro or azido, or a halogen atom, with an ester of a 7-alkoxymethyleneamino-$\Delta^3$-cephem-4-carboxylic acid obtained by reacting an ester of either formula VI or VII with a 1,1-dihalomethyl-alkyl ether, preferably 1,1-dichlorodimethyl ether, in the presence of a tertiary organic base; the reaction can be performed without isolation of the intermediate formed by the process, which in the example mentioned above is supposed to be a 7-N-methoxymethylene derivative of an ester of formula VI or VII. The reactions are performed below or at room temperature and in the presence of an inert solvent, e.g. chloroform, or ether. However, a more favourable method to obtain a 7-alkoxymethyleneamino-$\Delta^3$-cephem-4-carboxylic acid ester consists in reacting an ethereal solution of an ester of formula VI or VII with a formimidic ester hydrochloride, preferably isopropyl formimidic ester hydrochloride, preferably at room temperature and for the time necessary to accomplish the reaction. Ammonium chloride is thereby precipitated leaving an ethereal solution of a 7-alkoxymethyleneamino-$\Delta^3$-cephem-4-carboxylic acid ester.

The compounds of formula VIII are known compounds or they can be prepared analogous to the known compounds.

The reaction products of formula I can be purified and isolated in usual manner and may be obtained either in the free state or in the form of salts or esters. The free acids can also be obtained from the esters by chemical or enzymatic hydrolysis or a mild hydrogenolysis, and if the free acids are the reaction products, the salts and esters can be prepared therefrom by methods known from the literature.

By the preparation of esters of the compounds of the invention as well as the esters of the compounds of formula VI or VII especial attention must be drawn to the fact that the double bond in the ring structure under such reactions has a tendency to migrate from the preferred 3-position to the 2-position. As compounds having the double bond in the 2-position are of less value with respect to biological activity it will in most cases be advisable to use methods similar to that described in British Patent Specification No. 1 406 113, where the esterification process has been shown to run very quickly, when iodides are used in the esterification process instead of chlorides or bromides with the consequence that the migration is suppressed.

Another possible way of avoiding the double bond migration is in known way temporarily to form a sulfoxide derivative of the cephem compound in question.

Protection of an amino group

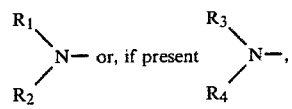

of the formula I and protection of a reactive amino radical attached to the carbon chain -A- in the formula I may, if necessary, take place by methods known from the peptide chemistry. Amongst many known and suitable protecting groups can be mentioned e.g. a benzyloxycarbonyl radical, a p-halo-, p-nitro-, or p-methoxybenzyloxycarbonyl radical, a $\beta,\beta,\beta$-trichloroethyloxycarbonyl or an allyloxycarbonyl radical; or a sulphur containing radical, such as a triphenylmethylsulphenyl radical, an arylsulphenyl radical, e.g. an o-nitrophenylsulphenyl radical; a triphenylmethyl radical, a tertiary butoxycarbonyl radical, or a radical obtained by reacting the free amino group with a $\beta$-dicarbonyl compound such as acetylacetone, benzoylacetone or acetoacetic esters or amides to form enamines, or to form Schiff bases with e.g. formaldehyde, acetaldehyde etc. In general any group which can be split off by reduction, by mild acid hydrolysis or by other mild reactions not damaging the $\beta$-lactam ring will be suitable. Also special attention should be drawn to the tendency of migration of the $\Delta^3$ double bond of the cephalosporanic acid derivatives. In general, when the reactions give rise to mixtures of $\Delta^2$ and $\Delta^3$ compounds, the $\Delta^3$-isomers can be isolated after chromatografic purification or by other methods as described in the literature, or preferably the mixture of $\Delta^2$ and $\Delta^3$ compounds can be transformed to a pure $\Delta^3$ compound via a sulfoxide by methods known from the literature.

Whatever protection of the amino group has been used or, alternatively, whatever conventional replacement of the amino group has been used, the amino group can be established by well-known methods, such as hydrogenation, hydrolysis or aminolysis.

In general, the compounds of formula I in which both $R_1$ and $R_2$ are hydrogen can be obtained from the corresponding nitro, azido or halo compounds by hydrogenation or aminolysis, respectively.

In another embodiment of the invention the compounds of the invention in which $R_1$ and/or $R_2$ are hydrogen can be exposed to acylation or alkylation by well-known methods to form the compounds of the invention in which $R_1$ and $R_2$ have the other desired definitions given hereinbefore.

Also the radical

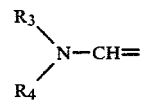

can optionally be introduced in a separate final step by methods analogous to the main reaction described above for obtaining the 7-amidino-$\Delta^3$-cephem-4-carboxylic acid structure.

Similarly, an amino group attached to the carbon chain -A- can be acylated or alkylated as above, or be introduced by converting e.g. an azido or nitro group or a halogen atom into an amino group followed, if desired, with an acylation or alkylation.

When by the above process a salt or an ester is obtained this can be transformed into the free acid in known manner and, vice versa, it will be evident that the free acid or a salt can be esterified by well-known methods.

According to one of these methods a compound of formula I can be transformed into the corresponding α-halo-alkyl ester, which then as an intermediate can be reacted with a salt of the acid in question to form e.g. an acyloxyalkyl ester, a symmetric or an assymetric ester of formula IV.

For technical reasons it may in some cases be preferable to exchange the $R_5'$ of the 3-substituents in the compounds of formula I, or the intermediates leading to the compounds of formula I, by means of a suitable nucleophilic displacement to obtain compounds of formula I having the desired substituent in the 3-position.

It is also an object of the present invention to provide an antibacterial pharmaceutical composition for use in the treatment of infectious diseases, which contains as an active ingredient a 7-amidino-$\Delta^3$-cephem-4-carboxylic acid derivative of the formula I given hereinbefore.

For parenteral and topical use the compounds of formula I or their salts are preferred. These can also in some cases be used orally. However, for oral use it is in most cases advantageous to use an easily hydrolyzable ester of the compounds, because such esters are generally better absorbed than the corresponding acids or salts. Some esters have less antibacterial activity per se, but they are during or after the absorption hydrolyzed with liberation of the corresponding free acids.

The active ingredient can be used as such or can be mixed up with a carrier and/or an auxiliary agent.

In such compositions, the proportion of therapeutically active material to carrier substance and auxiliary agent can vary between 1% and 95%. The compositions can either be worked up to pharmaceutical forms of presentation such as tablets, pills or dragees, or can be filled in medical containers such as capsules, or as far as suspensions are concerned filled into bottles. Pharmaceutical organic or inorganic solid or liquid carriers suitable for enteral, parenteral or topical administration can be used to make up the composition. Gelatine, lactose, starch, magnesium stearate, talc, vegetable and animal fats and oils, gum, polyalkylene glycol, or other known carriers for medicaments may all be suitable as carriers.

In the pharmaceutical compositions the compounds of the invention can be used together with other suitable therapeutically active components, preferably with other antibacterially active compounds, such as β-lactam-antibiotics, e.g. penicillins, amidinopenicillanic acid derivatives, cephalosporins or other amidinocephalosporanic acid derivatives. Also other antibacterially active substances are of interest in this connection, e.g. trimethoprim and aminoglycosides or other compounds as β-lactamase inhibitors, such as clavulanic acids. In such combinations a synergistic effect may be observed which can be of importance in many clinical situations without this enumeration being limiting for the invention. Also a depression of development of resistance can be obtained by a combination therapy. In such compositions the ratio between the active components appropriately is between 1:20 and 20:1, preferably within the ratio 1:5 and 5:1.

Another object of the invention resides in the selection of a dose of the compounds of the invention which can be administered so that the desired activity is achieved without simultaneous secondary effects.

The compounds are conveniently administered in dosage units containing amounts corresponding to from 0.025 g to 2.5 g of the free acid of formula I and preferably to from 0.05 g to 1.5 g depending on which microorganisms are involved. By the term "dosage unit" is meant a unitary, e.g. a single dose capable of being administered to a patient, and which may be readily handled and packed, remaining as a physically stable unit dose, comprising either the active material as such or a mixture of it with a pharmaceutical carrier.

Similarly, for infusion, the compounds of the invention are given in doses up to 10 g in aqueous solution.

For parenteral use, e.g. injections, the compounds of the invention are given e.g. in an aqueous solution or suspension as a dosage unit containing from 0.1 g to 1 g of the compound, calculated as the free acid to be dissolved or suspended immediately before use, or ready for use together with a pharmaceutically acceptable vehicle.

In the form of a dosage unit the compound may be administered once or more times a day at appropriate intervals, always depending, however, on the condition of the patient.

Thus, a daily dose will preferably amount to from 0.2 g to 30 g of the compound of the invention calculated as free acid.

The compounds of the invention are appropriately administered in the form of their pharmaceutically acceptable, non-toxic, easily hydrolyzable esters.

The term "non-toxic" for easily hydrolyzable esters shall mean that such esters are therapeutically acceptable for their intended form of administration. In general the easily hydrolyzable esters of the compounds of the invention are used in the oral administration, but their use in the parenteral administration is also within the scope of the invention.

The invention will be further described in the following Examples which are not construed as limiting the invention.

EXAMPLE 1

Pivaloyloxymethyl 7-[(4-(3-aminopropyl)-1-piperidyl)-methyleneamino]-3-methyl-3-cephem-4-carboxylate, dihydrochloride A. Pivaloyloxymethyl 7-[(4-(3-azidopropyl)-1-piperidyl)-methyleneamino]-3-methyl-3-cephem-4-carboxylate A solution of N-formyl-4-(3-azidopropyl)-piperidine (1.13 g) in alcohol-free chloroform (2.5 ml) was cooled to $-20°$ C. and oxalyl chloride (0.44 ml) in alcohol-free chloroform (2.5 ml) was added dropwise. After 1 hour at $-20°$ C. the solution was added dropwise at $-60°$ C. to $-70°$ C. to a stirred solution of pivaloyloxymethyl 7-amino-3-methyl-3-cephem-4-carboxylate (1.72 g) in alcohol-free chloroform (12 ml). Triethylamine (1.46 ml) was added and within the next hour the temperature was gradually raised to $-10°$ C. The solvent was evaporated and the residue was extracted with ether. The ether extract was evaporated to leave an oil, which was purified by column chromatography on Sephadex to yield the desired compound as a yellow oil.

The NMR-spectrum (CDCl$_3$, TMS as internal standard) showed peaks at $\delta=1.22$ (s); 0.9–2.0 (m); 2.08 (s); 2.6–4.1 (m); 3.30 (m); 3.26 (m); 4.95 (d, J=5); 5.12 (d, J=5); 5.9 (m); 7.53 (s) ppm.

B. Pivaloyloxymethyl 7-[(4-(3-aminopropyl)-1-piperidyl)-methyleneamino]-3-methyl-3-cephem-4-carboxylate, dihydrochloride To a stirred solution of pivaloyloxymethyl 7-[(4-(3-azidopropyl)-1-piperidyl)-methyleneamino]-3-methyl-3-cephem-4-carboxylate (1.5 g) in ethyl acetate (25 ml) were added water (30 ml) and hydrochloric acid to pH=3. 10% palladium-on-carbon (0.5 g) was added, and hydrogen was bubbled through the stirred mixture, a pH-value of 3 being maintained by addition of 0.2 N hydrochloric acid. When the consumption of acid ceased, the catalyst was filtered off. The aqueous phase was separated and freeze-dried to yield the desired compound as an amorphous powder.

The NMR-spectrum (CD$_3$OD, TMS as internal standard) showed peaks at $\delta = 1.20$ (s); 1.1–2.4 (m); 2.15 (s); 2.93 (m); 3.56 (m); 3.2–4.3 (m); 5.2–5.6 (m); 5.10 (d, J=5.5); 5.27 (d, J=5.5); 8.21 (s) ppm.

Antibiotic activity of the corresponding acid (obtained by treating the ester with mouse serum): (IC$_{50}$) against *E. coli* HA 2 Leo strain: 50 µg/ml.

EXAMPLE 2

Acetoxymethyl 7-[(4-(3-aminopropyl)-1-piperidyl)-methyleneamino]-cephalosporanate, dihydrochloride

A. Acetoxymethyl 7-[(4-(3-azidopropyl)-1-piperidyl)-methyleneamino]-cephalosporanate By following the method described above in step A, but substituting acetoxymethyl 7-amino-cephalosporanate for pivaloyloxymethyl 7-amino-3-methyl-3-cephem-4-carboxylate, the desired compound was obtained as a yellow oil.

The NMR-spectrum (CDCl$_3$, TMS as internal standard) showed peaks at $\delta = 0.9$–2.0 (m); 2.08 (s); 2.15 (s); 2.85 (bt); 3.85 (bd); 3.43 (m); 3.28 (t, J=6); 4.6–5.3 (m); 5.73 (s); 7.50 (s) ppm.

B. Acetoxymethyl 7-[(4-(3-aminopropyl)-1-piperidyl)-methyleneamino]-cephalosporanate, dihydrochloride By following the method described above in step B, but substituting acetoxymethyl 7-[(4-(3-azidopropyl)-1-piperidyl)-methyleneamino]-cephalosporanate for pivaloyloxymethyl 7-[(4-(3-azidopropyl)-1-piperidyl)-methyleneamino]-3-methyl-3-cephem-4-carboxylate, the desired compound was obtained as an amorphous powder.

The NMR-spectrum (CD$_3$OD, TMS as internal standard) showed peaks at $\delta = 1.0$–2.1 (m); 2.08 (s); 2.10 (s); 3.73 (m); 3.8–4.3 (m); 4.8–5.5 (m); 5.83 (m); 8.20 (s) ppm.

Antibiotic activity of the corresponding acid (obtained by treating the ester with mouse serum): (IC$_{50}$ against *E. coli* HA 2 Leo Strain: 5 µg/ml.

EXAMPLE 3

7-[(4-(3-aminopropyl)-1-piperidyl)-methyleneamino]-3-azidomethyl-3-cephem-4-carboxylic acid di-trifluoroacetate

A. N-Formyl-4-(3-aminopropyl)-piperidine hydrochloride

To a suspension of 10% palladium-on-carbon catalyst (3 g) in water (100 ml), a solution of N-formyl-4-(3-azidopropyl)-piperidine (19.6 g) in ethyl acetate (100 ml) was added. Hydrogen was passed through the mixture, and the pH was maintained at 3.0 by simultaneous addition of 1 N hydrochloric acid. When the consumption of acid ceased, the catalyst was filtered off, and the two layers separated. The aqueous phase was extracted twice with 25 ml portions of ethyl acetate, and thereafter evaporated to dryness in vacuo. The residue was dissolved in propanol-2, filtered, and the filtrate taken to dryness. The residue was treated with acetonitrile, and the crystals were filtered off and washed with acetonitrile followed by ether to give the title compound with m.p. 141°–143° C.

B. N-Formyl-4-(3-tert.-butoxycarbonylaminopropyl)-piperidine

To a stirred mixture of A (4.13 g), dry chloroform (40 ml) and triethylamine (2.8 ml), 2-tert.-butoxycarbonyloxyimino-2-phenyl-acetonitrile (4.9 g) was added in one portion. After stirring for 3 hours at room-temperature, the solvent was removed in vacuo, and the residue was treated with ether. Insoluble triethylamine hydrochloride was filtered off, and the filtrate was taken to dryness. The residue was chromatographed on silica gel. Elution with ether followed by ethyl acetate gave B as a colourless oil.

The IR-spectrum (chloroform) showed bands at 1700, 1655 and 1500 cm$^{-1}$.

C. 7-[(4-(3-tert.-butoxycarbonylaminopropyl)-1-piperidyl)-methyleneamino]-3-azidomethyl-3-cephem-4-carboxylic acid To a stirred suspension of 7-amino-3-azidomethyl-3-cephem-4-carboxylic acid (2.55 g) in dry chloroform (25 ml), trimethylchlorosilane (2.53 ml) was added. After stirring for 15 min., the mixture was cooled to 5° C., and triethylamine (2.8 ml) was added. Stirring was continued for 15 min. at room-temperature. The clear solution was cooled to −60° C., and a solution of the acid amide chloride, prepared from 3 g of B in chloroform (7 ml), and oxalylchloride (0.86 ml) in chloroform (3 ml) at −30° C., was added portionwise, maintaining a temperature of −60° C. Finally, triethylamine (2.8 ml) was added, and the mixture allowed to warm to 0° C. After stirring at 0° C. for 1 hour, the solvent was removed in vacuo, and the residue treated with dry ether (50 ml). Triethylamine hydrochloride was filtered off and washed with ether. The ether filtrate was stirred with water (100 ml) for 15 min. The aqueous layer was separated and freeze-dried to give C as a tan powder.

The IR-spectrum (chloroform) showed bands at 2100, 1760, 1690, 1630 and 1500 cm$^{-1}$.

D. 7-[(4-(3-aminopropyl)-1-piperidyl)-methyleneamino]-3-azidomethyl-3-cephem-4-carboxylic acid di-trifluoroacetate To a cooled suspension of C (1 g) in chloroform (5 ml), trifluoroacetic acid (5 ml) was added. After standing for 15 min., the clear solution was taken to dryness in vacuo. The residue was treated with water (50 ml), and insoluble matter was filtered off. The filtrate was freeze-dried to give D as an amorphous, hygroscopic powder.

The NMR-spectrum (D$_2$O, TMS as external standard) showed peaks at $\delta = 1.0$–2.1 (m), 2.95 (m), 3.65 (s), 4.00 (d, J=13), 4.45 (d, J=13), 3.0–4.0 (m), 5.21 (d, J=5), 5.58 (d, J=5), and 7.93 (s).

EXAMPLE 4

7-[(4-(3-aminopropyl)-1-piperidyl)-methyleneamino]-3-(1-methyl-1H-tetrazol-5-ylthiomethyl)-3-cephem-4-carboxylic acid, hydrochloride

A.

7-[(4-(3-azidopropyl)-1-piperidyl)-methyleneamino]-3-(1-methyl-1H-tetrazol-5-ylthiomethyl)-3-cephem-4-carboxylic acid A solution of N-formyl-4-(3-azidopropyl)-piperidine (0.96 g) in alcohol-free chloroform was cooled at −20° C. and oxalyl chloride (0.38 ml) was added dropwise. The solution was kept at −20° C. for 1 hour. The resulting solution was called (A).

In the meantime 7-amino-3-(1-methyl-1H-tetrazol-5-ylthiomethyl)-3-cephem-4-carboxylic acid (1.46 g) was suspended in alcohol-free chloroform (11 ml) and trimethylchlorosilane (1.13 ml) was added followed by triethylamine (1.25 ml). 1–2 minutes later a clear solution was obtained which quickly was cooled to −70° C. and the above prepared solution (A) was added dropwise at a temperature below −50° C. Then triethylamine (1.25 ml) was added below −50° C. and the stirring was continued for 1 hour while the temperature was allowed to raise to −10° C. The solvent was removed in vacuo and the residue was stirred with dry ether (50 ml). The suspension was filtered in the absence of moisture and isopropanol (2 ml) was added to the filtrate. The resulting suspension was stirred in an ice-bath for 1 hour and filtered to yield the desired compound as a light brown powder. The IR-spectrum (KBr) showed strong bands at 2090, 1760 and 1620–1595 cm$^{-1}$.

The NMR-spectrum (CF$_3$COOD, TMS as internal standard) showed peaks at δ=1.2–2.3 (m); 3.45 (bt); 3.93 (s); 4.22 (s); 3.3–4.2 (m); 4.1 (d); 4.71 (d, J=13); 5.32 (d, J=5); 5.70 (d, J=5) and 8.00 (bs) ppm.

B.

7-[(4-(3-aminopropyl)-1-piperidyl)-methyleneamino]-3-(1-methyl-1H-tetrazol-5-ylthiomethyl)-3-cephem-4-carboxylic acid, hydrochloride To a suspension of 7-[(4-(3-azidopropyl)-1-piperidyl)-methyleneamino]-3-(1-methyl-1H-tetrazol-5-ylthiomethyl)-3-cephem-4-carboxylic acid (0.65 g) in water (40 ml) were added 1 N hydrochloric acid to pH=2 and 5% Pd on barium sulphate (1 g). The mixture was shaken with hydrogen for half an hour and filtered. The filtrate was freeze-dried and the raw material thus obtained was purified by chromatography on a column of DIAION HP-20 packed in water. The column was eluted with water to yield fractions containing the desired compound. These fractions were pooled and freeze-dried to yield a colourless powder.

The NMR-spectrum (D$_2$O, TMS as external standard) showed peaks at δ=1.0–2.3 (m); 3.3–4.1 (m); 3.0 (bt); 3.70 (m); 4.20 (m); 4.05 (s); 5.22 (d, J=5); 5.53 (d, J=5) and 7.95 (bs) ppm.

EXAMPLE 5

7-[(4-(2-aminoethyl)-1-piperidyl)-methyleneamino]-cephalosporanic acid, monohydrochloride

A.

7-[(4-(2-azidoethyl)-1-piperidyl)-methyleneamino]-cephalosporanic acid

A solution of N-formyl-4-(2-azidoethyl)-piperidine (2.00 g) in alcohol-free chloroform (20 ml) was cooled to −20° C. and a solution of oxalyl chloride (0.84 ml) in alcohol-free chloroform (10 ml) was added dropwise. The mixture was kept at −20° C. for 1 hour. The resulting solution is called (A).

7-aminocephalosporanic acid (2.72 g) was suspended in alcohol-free chloroform (30 ml) and trimethylchlorosilane (2.52 ml) was added. After stirring for 15 minutes the mixture was cooled to 0° C. and triethylamine (2.80 ml) was added. The heat of reaction raised the temperature to about 20° C. and an almost clear solution was obtained in a few minutes. After stirring for 30 minutes at room temperature the solution was cooled to −70° C. and the above prepared solution (A) was added dropwise at a temperature below −60° C. Triethylamine (2.80 ml) was added still at −60° C., and within the next hour the temperature was gradually raised to −10° C. The solvent was evaporated off and the residue was stirred with dry ether (80 ml) for 3 minutes. The precipitate was filtered off and the filtrate cooled in an ice-bath. Water (40 ml) was added with vigorous stirring and stirring was continued for 10 minutes. The aqueous layer was separated, filtered and freeze-dried to yield a yellowish amorphous powder, which crystallized from methanol/propanol-2. The crystals were filtered off, washed with propanol-2 and dried in vacuo. Melting point 163°–164° C. dec.

The NMR-spectrum (D$_2$O/C$_5$D$_5$N 2:1, TMS as internal tandard) showed peaks at δ=1.1–2.1 (m); 2.25 (s); 3.37 (m); 3.67 (ABq); 3.1–4.3 (m); 5.13 (s); 5.53 (d, J=5); 5.91 (d, J=5); 8.23 ppm.

B.

7-[(4-(2-aminoethyl)-1-piperidyl)-methyleneamino]-cephalosporanic acid, monohydrochloride 7-[(4-(2-azidoethyl)-1-piperidyl)-methyleneamino]-cephalosporanic acid (1.0 g) was dissolved in water (35 ml) by addition of 1 N hydrochloric acid to a pH-value of 2.0. 10 percent palladium on carbon catalyst (1.0 g) was added and hydrogen was bobbled through the stirred mixture for 30 minutes. The pH-value of the mixture raised gradually to 3.1 and stopped at this value. The catalyst was filtered off and the filtrate was freeze-dried to yield the desired compound as a colourless amorphous powder.

The NMR-spectrum (D$_2$O, TMS as external standard) showed peaks at δ=1.1–2.1 (m); 2.13 (s); 3.07 (m); 3.62 (ABq); 3.2–4.1 (m); 4.75 (d, J=14); 4.93 (d, J=14); 5.23 (d, J=5); 5.60 (bd, J=5); 8.00 (bs) ppm.

EXAMPLE 6

7-[(4-aminomethyl-1-piperidyl)-methyleneamino]-cephalosporanic acid, monohydrochloride

A.

7-[(4-azidomethyl-1-piperidyl)-methyleneamino]-cephalosporanic acid

This compound was prepared as described in Example 5, step A by substituting N-formyl-4-azidomethylpiperidine for N-formyl-4-(2-azidoethyl)-piperidine. It was crystallized from methanol/propanol-2. Melting point 157°–160° C. dec.

The NMR-spectrum (D$_2$O, TMS as external standard) showed peaks at δ=1.2–2.1 (m); 2.08 (s); 3.30 (d, J=5.5); 3.55 (ABq); 3.2–4.2 (m); 4.70 (d, J=14); 4.88 (d, J=14); 5.22 (d, J=5); 5.88 (d, J=5); 8.00 (s) ppm.

B.

7-[(4-aminomethyl-1-piperidyl)-methyleneamino]-cephalosporanic acid, monohydrochloride To a solution of 7-[(4-azidomethyl-1-piperidyl)-methyleneamino]-cephalosporanic acid (1.0 g) in water (40 ml) were added 10 percent palladium on carbon (1.0 g) and hydrochloric acid to pH=3. Hydrogen was bubbled through the stirred mixture, a pH-value of 3 being maintained by the addition of hydrochloric acid. When the consumption of acid ceased the catalyst was filtered off and the filtrate was freeze-dried to yield the desired compound as a colourless amorphous powder.

The NMR-spectrum (D$_2$O, TMS as external standard) showed peaks at δ=1.2–2.2 (m); 2.12 (s); 3.00 (d, J=7); 3.62 (ABq); 3.2–4.1 (m); 4.83 (ABq); 5.23 (d, J=5); 5.60 (d, J=5); 8.00 (bs) ppm.

EXAMPLE 7

7-[(4-(3-aminopropyl)-1-piperidyl)-methylenamino]-cephalosporanic acid hydrochloride By replacing N-formyl-4-(2-azidoethyl)-piperidine with N-formyl-4-(3-azidopropyl)-piperidine in Example 5 and proceeding in analogous manner the intermediate azido-compound was obtained as crystals with melting point 135° C. dec. from propanol-2. The IR-spectrum (potassium bromide) showed strong bands at 2100, 1760, 1730, 1685 and 1635–1600 cm$^{-1}$.

The title compound was obtained as an amorphous solid.

The NMR-spectrum (D$_2$O, TMS as external standard) showed peaks at δ=1.1–2.0 (m); 2.12 (s); 3.03 (m); 3.62 (ABq); 3.2–4.0 (m); 4.85 (ABq, J=13); 5.25 (d, J=5); 5.60 (d, J=5) and 8.02 (bs).

EXAMPLE 8

7-[(4-(3-azidopropyl)-1-piperidyl)-methyleneamino]-3-(1,2,3-triazol-5-ylthiomethyl)-3-cephem-4-carboxylic acid A solution of N-formyl 4-(3-azidopropyl)-piperidine (1.08 g ~ 5.5 mmol) in alcohol-free chloroform (10 ml) was cooled to −20° C. and a solution of 0.42 ml oxalyl chloride in 5 ml alcohol-free chloroform was added dropwise. The mixture was kept af −20° C. for 1 hour. (Solution A).

1.56 g (5 mmol) 7-amino-3-(1,2,3-triazol-5ylthiomethyl)-3-cephem-4-carboxylic acid was suspended in 60 ml of alcohol-free chloroform. The mixture was cooled to −10° C. and 2.89 ml (15 mmol) of trimethylchlorosilane was added. After stirring for 15–20 minutes, 2.1 ml ~ (15 mmol) of triethylamine was added quickly. The heat of reaction raised the temperature to about 15° C. and a clear solution was obtained after about 20 minutes. The solution was cooled to −70° C. and solution A was added dropwise at a temperature below −60° C.; triethylamine (1.40 ml ~ 10 mmol) was added still at −60° C. Within the next hour the temperature was raised to −10° C., the solvent was evaporated in vacuo and the residue was extracted with dry ether (2 × 100 ml). The extract was filtered and cooled, 3 ml of methanol was added with stirring, the resulting milky suspension was evaporated in vacuo and a yellow amorphous powder was obtained.

IR: 2100 cm$^{-1}$, 1780 cm$^{-1}$, 1695 cm$^{-1}$, and 1610 cm$^{-1}$.

EXAMPLE 9

7-[(4-(2-Azidoethyl)-1-piperidyl)methyleneamino]-3-(5-methyl-1,3,4-thiadiazol-2-ylthiomethyl)-3-cephem-4-carboxylic acid, hydrochloride A solution of oxalyl chloride (0.43 ml) in alcohol-free chloroform (5 ml) was added dropwise to a stirred solution of 4-(2-azidoethyl)-1-formylpiperidine (1.0 g) in chloroform (5 ml) at −20° C. The stirring was continued for one hour at −20° C.

Meanwhile a suspension of 7-amino-3-(5-methyl-1,3,4-thiadiazol-2-ylthiomethyl)-3-cephem-4-carboxylic acid in chloroform (15 ml) was stirred for 15 minutes with trimethylchlorosilane (1.26 ml) at room temperature. Without cooling, triethylamine (1.4 ml) was added. After stirring for 10 minutes, the resulting solution was cooled to −70° C.

To this solution the solution of the amide chloride was added during 10 minutes followed by the addition of triethylamine (1.4 ml) during 10 minutes. The temperature was raised to 0° C. during one hour and maintained at 0° C. for another hour. After evaporation in vacuo the residue was extracted with ethyl ether (30 ml). The undissolved material was filtered off and washed with ethyl ether (2×25 ml). To the ethereal solution isopropanol (0.8 ml) was added at 0° C. The reaction mixture was kept at 0° C. during the night and filtered.

To the crude product in n-propanol (12 ml) was added 0.21 ml of a solution of hydrogen chloride in isopropanol (8 N) followed by the addition of ethyl ether (50 ml). The crude salt was isolated and suspended in ethyl ether (25 ml). After filtration it was recrystallized from n-propanol-ethyl ether and ethanol-ethyl ether to yield the analytically pure compound with m.p. 163°–165° C. (dec.)

[α]$_D^{20}$: −152° (c:1. 96% C$_2$H$_5$OH).

NMR spectrum: δ=1.0–2.2 (m); 2.72 (s); 3.40 (t, J=7); 3.86 (ABq); 3.3–4.2 (m); 4.33 (d, J=13); 4.58 (d, J=13); 5.22 (d, J=5); 5.63 (d, J=5); 8.22 (bs) ppm.

EXAMPLE 10

7-[(4-(3-Azidopropyl)-1-piperidyl)methyleneamino]-3-(5-methyl-1,3,4-thiadiazol-2-ylthiomethyl)-3-cephem-4-carboxylic acid, hydrochloride This compound was prepared by following the procedure of Example 9 and substituting 4-(3-azidopropyl)-1-formylpiperidine for 4-(2-azidoethyl)-1-formylpiperidine. M.p. 160°–165° C. (dec.) from n-propanol-ethyl ether.

[α]$_D^{20}$: −151° (c:1, 96% C$_2$H$_5$OH).

NMR spectrum: δ=1.0–2.2 (m); 2.73 (s); 3.85 (ABq); 3.34 (m); 3.2–4.2 (m); 4.34 (d, J=13); 4.58 (d, J=13); 5.25 (d, J=5); 5.65 (d, J=5); 8.23 (s) ppm.

What we claim is:

1. An antibiotic compound of the formula

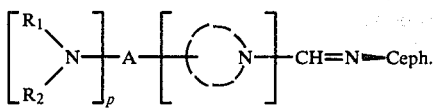   I in which the radical

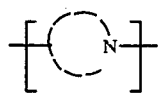

stands for the groupings:

   II

, 20 representing saturated, monocyclic, bicyclic or spirocyclic ring systems, respectively, having from 4 to 11 carbon atoms in total; —A— stands for a straight or branched, saturated or unsaturated $C_1$ to $C_6$ aliphatic hydrocarbon radical optionally including a phenyl moiety, and where —A— optionally can be substituted with an amino radical; $R_1$ stands for hydrogen, or lower alkyl having from 1 to 4 carbon atoms; $R_2$ stands for hydrogen, lower alkyl or monoacyl derived from a mono- or dibasic carboxylic acid, sulphuric acid, a sulphonic acid, a sulphinic acid, phosphoric acid, or a phosphonic acid, or $R_2$ is a radical selected from the group consisting of carbamoyl, guanyl and guanylcarbamoyl radicals which are unsubstituted or substituted with lower alkyl or phenyl; or $R_1$ and $R_2$ together with the nitrogen atom form a monocyclic, saturated ring having from 4 to 8 carbon atoms or an azido group; or $R_1$ and $R_2$ together represent a radical of the formula

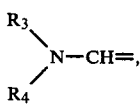

in which $R_3$ and $R_4$ each stands for hydrogen, lower alkyl, phenyl or phenyl-lower-alkyl, or in which $R_3$ and $R_4$ together with the nitrogen atom form a monocyclic, saturated ring having from 4 to 8 carbon atoms; p is 1, and when A includes an aryl moiety, p is 0 or 1; Ceph. stands for the $\Delta^3$-cephem-4-carboxylic acid radical of the formula III

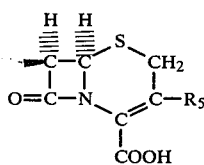   III in which $R_5$ is halogen, methoxy or the group —CH=CH—COOH, or a $CH_2R'_5$ group representing a 3-position substituent of the 7-acylamino-$\Delta^3$-cephem-4-carboxylic acid series; non-toxic salts of the compounds of the formula I with pharmaceutically acceptable, non-toxic acids or bases; or pharmaceutically acceptable, non-toxic, esters of the compounds of formula I.

2. A compound as claimed in claim 1, wherein $R'_5$ is hydrogen, halogen, hydroxy, alkoxy, alkanoyloxy, a carbamoyloxy radical, alkylthio, methyltetrazolylthio, triazolylthio, or methylthioadiazolylthio, trialkylammonium, a pyridinium radical, a rhiuronium group, amidinothio optionally substituted at the nitrogen atoms with $C_1$ to $C_3$ alkyl groups, N-substituted aminothiocarbonylthio, phenylthio, alkoxythio-carbonylthio, alkylphenylsulfonyl, azido, amino or amido, polyhydroxyphenyl, indol-3-yl optionally substituted at the nitrogen atom with $C_1$ to $C_3$ alkyl groups, or thiocyano.

3. An antibiotic of the formula

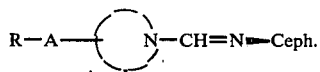   Ia in which the radical

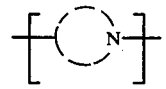

stands for pyrrolidyl, piperidyl, hexahydroazepinyl or octahydroazocinyl, R stands for amino or azido; —A— stands for a straight or branched, saturated or unsaturated $C_1$ to $C_6$ aliphatic hydrocarbon radical; Ceph. stands for the $\Delta^3$-cephem-4-carboxylic acid radical of the formula III

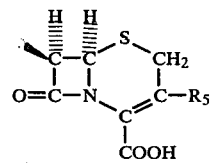   III in which $R_5$ is halogen, methoxy or the group —CH=CH—COOH, or a $CH_2R'_5$ group represents a 3-position substituent of the 7-acylamino-$\Delta^3$-cephem-4-carboxylic acids, non-toxic salts of the compounds of the formula I with pharmaceutically acceptable, non-toxic acids or bases, pharmaceutically acceptable, non-toxic, esters of the compounds of formula I; or salts of such esters with pharmaceutically acceptable, non-toxic acids or bases.

4. A compound as in claim 1, wherein p is 1, $R_1$ and $R_2$, when they together represent a radical of the formula

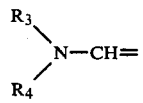

then $R_3$ and $R_4$ each stands for hydrogen, lower alkyl, phenyl or phenyl-lower alkyl, or $R_3$ and $R_4$ together with the nitrogen atom form a monocyclic, saturated ring having from 4 to 7 carbon atoms, and $R_5$ represents the group $CH_2R'_5$.

5. A compound as in claim 1 wherein the radical

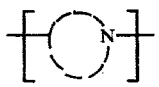

stands of the grouping

representing a saturated monocyclic ring with 4 to 11 carbon atoms.

6. A compound as in claim 5 wherein $R_1$ and $R_2$ is hydrogen or lower alkyl with 1 to 4 carbon atoms or $R_1$ and $R_2$ together with the nitrogen atom can form an azido group, A is a straight or branched saturated $C_1$ to $C_6$ aliphatic hydrocarbon radical optionally substituted with a phenyl group, A optionally being substituted with an unsubstituted or mono- or di-lower alkyl substituted amino group, the

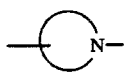

grouping represents a saturated monocyclic ring with 4–7 carbon atoms and $R'_5$ is hydrogen, acetoxy, 2-methyl-1,3,4-thiadiazol-5-yl-thio, 1-methyl-1H-tetrazol-5-yl-thio, 1,2,3-triazol-5-yl-thio, 5-methyl-1,3,4-thiadiazol-2-yl-thio, 1-pyridinium, azido, carbamyl, 1,2,5,6-tetrahydro-2-methyl-5,6-dioxo-as-triazin-3-yl-thio or 1,4,5,6-tetrahydro-4-methyl-5,6-dioxo-as-triazin-3-yl-thio.

7. A compound as in claim 6 wherein $R_1$ and $R_2$ are hydrogen or methyl or together with the nitrogen atom an azido group.

8. A compound as in claim 7 wherein $R_1$ and $R_2$ are both hydrogen.

9. A compound as in claim 8 wherein A is methylene, ethylene or propylene.

10. A compound as in claim 9 wherein the

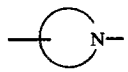

grouping represents piperidyl-1.

11. A compound as in claim 9 wherein the

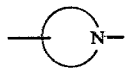

grouping represents hexahydro-1H-azepin-1-yl.

12. 7-[(4-(3-Aminopropyl)-1-piperidyl)-methyleneamino]-3-methyl-3-cephem-4-carboxylic acid, non-toxic, pharmaceutically acceptable esters thereof or pharmaceutically acceptable, non-toxic salts of said acid or said esters.

13. 7-[(4-(3-Aminopropyl)-1-piperidyl)-methyleneamino]-cephlosporanic acid, non-toxic, pharmaceutically acceptable esters thereof or pharmaceutically acceptable, non-toxic salts of said acid or said esters.

14. 7-[(4-(3-Aminopropyl)-1-piperidyl)-methyleneamino]-3-azido-methyl-3-cephem-4-carboxylic acid, non-toxic, pharmaceutically acceptable esters thereof or pharmaceutically acceptable, non-toxic salts of said acid or said esters.

15. 7-[(4-(3-Aminopropyl)-1-piperidyl)-methyleneamino]-3-(1-methyl-1H-tetrazol-5-ylthiomethyl)-3-cephem-4-carboxylic acid, non-toxic, pharmaceutically acceptable esters thereof or pharmaceutically acceptable, non-toxic salts of said acid or said esters.

16. 7-[(4-(2-Aminoethyl)-1-piperidyl)-methyleneamino]-cephalosporanic acid, non-toxic, pharmaceutically acceptable esters thereof or pharmaceutically acceptable non-toxic salts of said acid or said esters.

17. 7-[(4-Aminomethyl-1-piperidyl)-methyleneamino]-cephalosporanic acid, non-toxic, pharmaceutically acceptable esters thereof or pharmaceutically acceptable, non-toxic salts of said acid or said esters.

18. 7-[(4-(3-Aminopropyl)-1-piperidyl)-methylenamino]-cephalosporanic acid, non-toxic, pharmaceutically acceptable esters thereof or pharmaceutically acceptable, non-toxic salts of said acid or said esters.

19. 7-[(4-(3-Aminopropyl)-1-piperidyl)-methyleneamino]-3-(1,2,3-triazol-5-ylthiomethyl)-3-cephem-4-carboxylic acid, non-toxic, pharmaceutically acceptable esters thereof or pharmaceutically acceptable, nontoxic salts of said acid or said esters.

20. 7-[(4-(2-Azidoethyl)-1-piperidyl)methyleneamino]-3-(5-methyl-1,3,4-thiadiazol-2-ylthiomethyl)-3-cephem-4-carboxylic acid, non-toxic, pharmaceutically acceptable esters thereof or pharmaceutically acceptable, nontoxic salts of said acid or said esters.

21. 7-[(4-(3-Azidopropyl)-1-piperidyl)-methyleneamino]-3-(5-methyl-1,3,4-thiadizaol-2-ylthiomethyl)-3-cephem-4-carboxylic acid, non-toxic, pharmaceutically acceptable esters thereof or pharmaceutically acceptable, non-toxic salts of said acid or said esters.

22. 7-[(4-(3-Azidopropyl)-1-piperidyl)-methyleneamino]-3-methyl-3-cephem-4-carboxylic acid, non-toxic, pharmaceutically acceptable esters thereof or pharmaceutically acceptable, non-toxic salts of said acid or said esters.

23. 7-[(4-(3-Azidopropyl)-1-piperidyl)-methyleneamino]-cephalosporanic acid, non-toxic, pharmaceutically acceptable esters thereof or pharmaceutically acceptable, non-toxic salts of said acid or said esters.

24. An antibacterial composition comprising an effective amount of a compound according to claim 1, and a carrier.

25. Method for combatting or preventing infection diseases which comprises administering an effective amount of a compound according to claim 1.

* * * * *